United States Patent
Wang et al.

(10) Patent No.: US 12,258,449 B2
(45) Date of Patent: Mar. 25, 2025

(54) PHOTOCURABLE COMPOSITIONS HAVING VARIABLE VISCOSITIES

(71) Applicant: AGENCY FOR SCIENCE, TECHNOLOGY AND RESEARCH, Singapore (SG)

(72) Inventors: Fuke Wang, Singapore (SG); Chaobin He, Singapore (SG); Fei Wang, Singapore (SG); Yi Ting Chong, Singapore (SG)

(73) Assignee: AGENCY FOR SCIENCE, TECHNOLOGY AND RESEARCH, Singapore (SG)

(*) Notice: Subject to any disclaimer, the term of this patent is extended or adjusted under 35 U.S.C. 154(b) by 659 days.

(21) Appl. No.: 17/610,738

(22) PCT Filed: May 15, 2020

(86) PCT No.: PCT/SG2020/050282
§ 371 (c)(1),
(2) Date: Nov. 12, 2021

(87) PCT Pub. No.: WO2020/231341
PCT Pub. Date: Nov. 19, 2020

(65) Prior Publication Data
US 2022/0267529 A1 Aug. 25, 2022

(30) Foreign Application Priority Data
May 15, 2019 (SG) .......................... 10201904366Y

(51) Int. Cl.
*C08G 77/04* (2006.01)
*A61K 6/17* (2020.01)
(Continued)

(52) U.S. Cl.
CPC .............. *C08G 77/045* (2013.01); *A61K 6/17* (2020.01); *A61K 6/62* (2020.01); *B33Y 70/00* (2014.12)

(58) Field of Classification Search
CPC ..................................................... A61K 6/887
See application file for complete search history.

(56) References Cited

U.S. PATENT DOCUMENTS 6,313,192 B1 * 11/2001 Anstice ................... C04B 28/28
524/549
6,664,024 B1 12/2003 Nguyen et al.
(Continued)

FOREIGN PATENT DOCUMENTS

| CN | 108117624 A | 6/2018 |
| KR | 2019-0001791 A | 1/2019 |
| WO | WO-2018/122424 A1 | 7/2018 |

OTHER PUBLICATIONS

Isobonyl methacrylate data, Alfa Chemistry, 2024. (Year: 2024).*
(Continued)

*Primary Examiner* — Michael F Pepitone
(74) *Attorney, Agent, or Firm* — MARSHALL, GERSTEIN & BORUN LLP

(57) ABSTRACT

Photocurable compositions comprising 20-90% by weight of a polymerizable core resin; 20-90% by weight of a diluent resin miscible with said core resin; and at least about 1% by weight of at least one rheology modifier which is distinct from said diluent resin. Rheology modifiers of the present disclosure include compounds which may form covalent bonds with the core resin or diluent resin and compounds which have a particle size of 1-200 nm. Rheology modifiers which may form covalent bonds have at least one terminal (Continued)

functional group selected from the group consisting of acrylates, methacrylates, epoxides, oxetanes, nitriles, alkenes and alkynes.

13 Claims, 1 Drawing Sheet

(51) Int. Cl.
  *A61K 6/62* (2020.01)
  *B33Y 70/00* (2020.01)

(56) References Cited

U.S. PATENT DOCUMENTS

| | | |
|---|---|---|
| 2008/0287564 A1 | 11/2008 | Klare et al. |
| 2011/0135749 A1* | 6/2011 | Sellinger ............. C08K 5/5425 424/676 |
| 2016/0324730 A1 | 11/2016 | Lee |

OTHER PUBLICATIONS

International Search Report in International Application No. PCT/SG2020/050282 dated Jul. 15, 2020, 6 pages.
International Preliminary Report on Patentability in International Application No. PCT/SG2020/050282 dated Jul. 16, 2021, 21 pages.

* cited by examiner

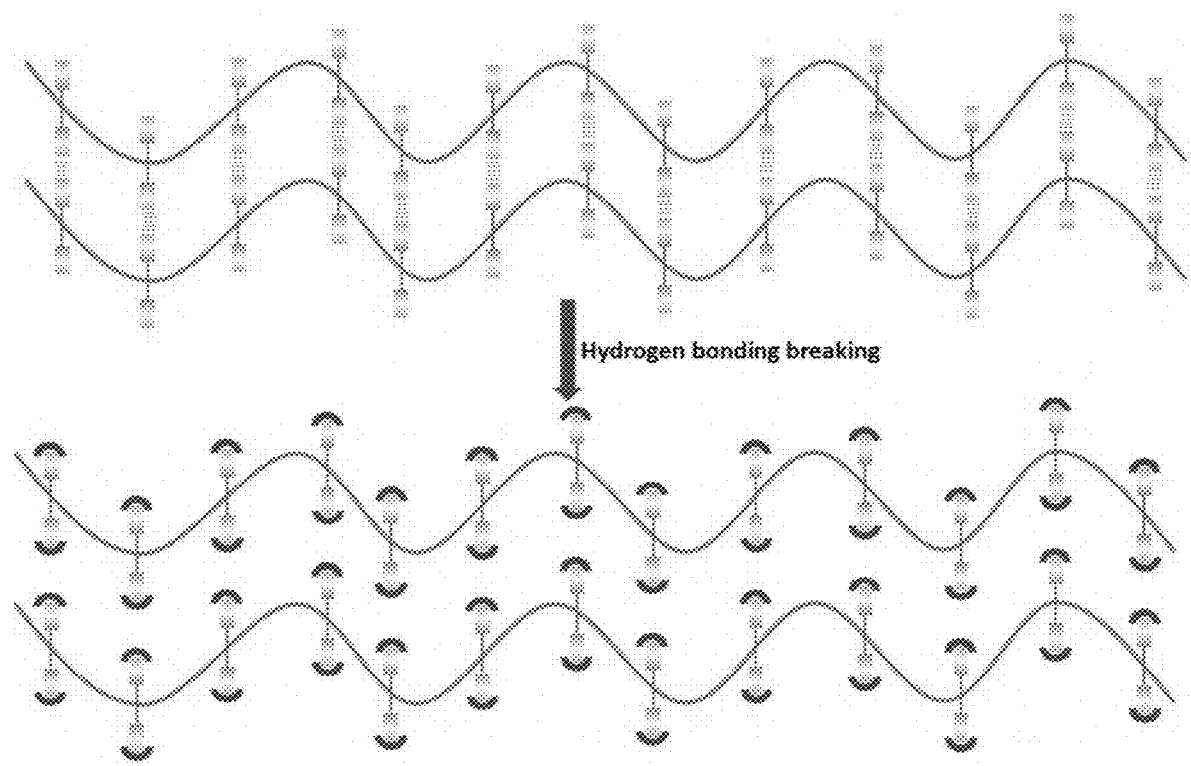

PHOTOCURABLE COMPOSITIONS HAVING VARIABLE VISCOSITIES

CROSS-REFERENCE TO RELATED APPLICATION

The present disclosure is a national phase application of PCT Patent Application No. PCT/SG2020/050282 filed May 15, 2020, which claims the priority benefit of Singapore patent Application No. 10201904366Y filed May 15, 2019, the entire respective disclosures of which are incorporated herein by reference.

TECHNICAL FIELD

The present invention relates to compositions having additives for the adjustment of viscosity, its methods for preparation and uses thereof.

BACKGROUND ART

Dental diseases remain a major public health concern in developing nations as it affects 60-90% of school-aged children and a vast majority of adults. However, traditional restorative, corrective and dental filling techniques are often time consuming and expensive. The development of three dimensional (3D) printing techniques makes possible the printing of dental structures, which provides an alternative for the treatment of dental diseases. The printing of various dental structures, such as implants, surgical guides, braces, dentures, crowns and bridges are of great interest in the dental industry.

The interest in 3D printing of dental structures also leads to renewed interest in the materials and compositions which may be used to print these structures. Materials which may be used for dental 3D printing include metals, photopolymers, and ceramics. At present, photopolymer materials are most commonly used due to its low cost and ability to be molded to various dental models.

Suitable materials for use in dental 3D printing should fulfil a number of requirements. For instance, such materials should be biocompatible and possess a good balance between mechanical strength and viscosity. Several materials such as TPH3 and Opallis are currently commercially available for such dental printing applications. However, while these materials exhibit good mechanical strength, their high viscosity of about 10,000-18,000 mPa·s renders them unsuitable for use in 3D printing.

Liquid-based 3D printing techniques such as Stereolithography (SLA) and Digital Light Processing (DLP) require a resin to be of low viscosity to ensure fast filling of each layer during printing and for high printing resolution of the polymerized resin. Compositions to be used for liquid-based 3D printing should preferably have a viscosity of less than 200 mPa·s.

Photocurable compositions which are used for 3D printing generally contain a core resin such as Bisphenol A glycidyl methacrylate (Bis-GMA). The chemical structure of Bis-GMA is as below:

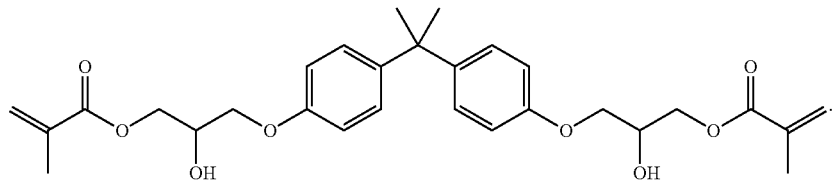 [SMILES: C=C(C)C(=O)OCC(O)COc1ccc(C(C)(C)c2ccc(OCC(O)COC(=O)C(=C)C)cc2)cc1]

One of the drawbacks of using Bis-GMA is its high viscosity (1.0-1.2 kPa·s at 23° C.) in the liquid state.

Other alternative core resins include poly(ethylene glycol) diacrylate (PEGDA) and 1,6-Hexanediol diacrylate (HDDA). The chemical structures of PEGDA (left) and HDDA (right) are as follows:

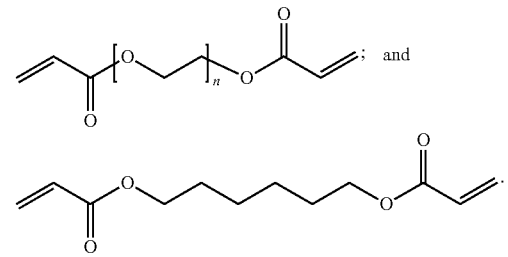

While such resins have lower viscosity as compared to Bis GMA, resulting polymers often do not meet the mechanical strength requirement for dental structures. In addition, such compositions also exhibit volumetric shrinkage during polymerization. This necessitates the addition of nanofillers at about 50 vol. % to reduce volumetric shrinkage of the composition. However, the addition of nanofillers is disadvantageous as it increases the viscosity of the composition, and interferes with the absorption of light during photocuring.

A common approach which has been adopted to reduce the viscosity of the composition is to add diluent resins of lower viscosity to Bis-GMA. However, a large amount of diluent resin is often required (>50 wt %) to achieve the desired viscosity for 3D printing. It has been found that the large quantity of diluent resin which is required compromises the mechanical strength of the cured polymer.

Accordingly, there is a need to provide a photocurable composition for liquid-based dental 3D printing, which not only exhibits low viscosity, but also possesses high mechanical strength and does not exhibit volumetric shrinkage upon curing.

SUMMARY OF INVENTION

In one aspect of the present disclosure, there is provided a photocurable composition comprising 20-90% by weight of a polymerizable core resin; 20-90% by weight of a diluent resin which is miscible with said core resin; and at least about 1% by weight of at least one rheology modifier, said rheology modifier being distinct from said diluent resin, wherein the total amount of (i), (ii), and (iii) is between 90 wt. % to 100 wt. % of the photocurable composition; and wherein the rheology modifier is a compound of general formula I:

$$A\text{-}P_n \quad \text{Formula I}$$

wherein A is selected from the group consisting of optionally substituted alkyl, optionally substituted alkenyl, optionally substituted aryl group, optionally substituted alkoxy and optionally substituted organosilicon polymer;

P is optionally present, and is a polymerizable terminal functional group capable of covalently bonding to said core resin, or said diluent resin, or both; and wherein P is, in each instance, independently selected from the group consisting of acrylates, methacrylates, epoxides, oxetanes, nitriles, alkenes and alkynes; and where P is present, n is an integer of between 1 to 20.

In another aspect, there is provided a photocurable composition comprising 20-90% by weight of a polymerizable core resin; 20-90% by weight of a diluent resin miscible with said core resin; and at least about 1% by weight of at least one rheology modifier. The rheology modifier may have a size of about 1-200 nm and the total amount of the core resin, diluent resin and rheology modifier is between 90 to 100% by weight of said photocurable composition.

Advantageously, the incusion of about 1 wt % of at least one rheology modifier may allow a desired viscosity of the photocurable composition to be achieved. The viscosity of the photocurable composition disclosed herein may be at least 2 times lower as compared to photocurable compositions which do not contain a rheology modifier as defined herein. Surprisingly, the photocurable composition is able to retain its mechanical, tensile and compressive strength upon curing, despite its low viscosity in the liquid state.

Also advantageously, the photocurable composition disclosed herein is of low viscosity without experiencing an unacceptable impairment in physical strength. In preferred embodiments, the viscosity of the photocurable compositions disclosed herein is lower than about 550 mPa·s, preferably lower than about 60 mPa·s at 25° C. The low viscosity of the compositions may be attributed to the presence of rheology modifiers which may be able to disrupt the non-covalent interactions in the composition.

The disruption of non-covalent interactions in the composition may occur through the formation of new non-covalent interactions between the substituents of the rheology modifier and the core resin and/or diluent resin. In embodiments, the addition of rheology modifiers may disrupt the hydrogen bonding interactions in the composition. The disruption of hydrogen bonding interactions may occur through the formation of new hydrogen bonds between the polar substituents of the rheology modifier and the polar substituents of the core resin; or diluent resin; or both the core resin and diluent resin. The disruption of hydrogen bonding may also occur by increasing the space or distance between the alkyl chains of the core resin and/or diluent resin. This may reduce the degree of hydrogen bonding in the core resin, which leads to a reduction in viscosity of the photocurable composition.

Definitions

The following words and terms used herein shall have the meaning indicated:

The term 'photocurable' as used herein refers to compounds or compositions which may be cured, hardened or polymerized using visible or ultraviolet light. The exposure of monomers or oligomers with specific reactive functional groups to visible or ultraviolet light may result in the formation of intermolecular and intramolecular covalent linkages. This may result in the hardening of monomeric or oligomeric substrates or both, allowing the formation of polymer matrices.

The term 'neat' as used herein refers to liquid or liquid compositions which do not comprise solvents or fillers.

The term 'monomer' as used herein refers to a compound which may react chemically with other molecules which may or may not be of the same type to form a larger molecule. Monomers may comprise functional groups capable of forming covalent linkages and reacting with other molecules.

The term 'oligomer' as used herein refers to compounds which comprise repeating units of at least one monomer. Oligomers may contain less than 20 repeating units of a monomer. Examples of oligomers include dimers, trimers and tetramers which contain 2, 3 and 4 units of one or more monomers, respectively.

The term "polymer" as used herein refers to compounds which comprise multiple repeating units of a monomer. Polymers may be longer than oligomers and may comprise an infinite number of repeating units of a monomer. Polymers have long chains of repeating units and have high molecular weight.

The term "spherical" as used herein may refer to modifiers which occupy a substantially round three-dimensional space. Spherical modifiers may have a surface or perimeter on which every point is of a substantially equal distance from the center of the molecule. Examples of spherical modifiers may be nanoparticles or branched compounds.

The term "hybrid nanoparticle" as used herein may refer to nanoparticles which are composed of inorganic and organic groups or materials. Hybrid nanoparticles may be inorganic nanoparticles substituted with alkyl groups. Examples of hybrid nanoparticles include silicon dioxide nanoparticles substituted with poly(ethylene glycol) linkers.

The term "hybrid cage molecules" as used herein may refer to three dimensional, ordered inorganic structures which may be substituted with inorganic or organic moieties. Such cage molecules may be symmetric or non-symmetric in nature and may occupy a significant volume. Examples of "hybrid cage molecules" may include metal-organic frameworks and polyhedral oligomeric silsesquioxane cage molecules.

The term "homogenous" as used herein refers to mixtures which contain a uniform distribution of components throughout. Homogenous mixtures may have the same composition of components throughout. Homogenous mixtures may contain only one phase of matter, e.g. only liquid, solid or gas.

The term "optionally substituted" as used herein means the group to which this term refers may be unsubstituted, or may be substituted with one or more groups independently selected from —$C_1$-$C_{20}$-alkyl, —$C1$-$C_{20}$-alkenyl, —$C_1$-$C_{20}$-alkynyl, —$C_3$-$C_{20}$-cycloalkyl, —$C_5$-$C_{20}$-cycloalkenyl, —$C_5$-$C_{20}$-heterocycloalkyl having 1 to 5 hetero atoms selected from N, O and S in the ring, halo, —$C_1$-$C_{20}$-haloalkyl.

"Alkyl" as a group or part of a group refers to a straight or branched aliphatic hydrocarbon group, particularly but not limited to, at least one carbon atom, or a $C_1$-$C_{20}$ alkyl, a $C_1$-$C_{10}$ alkyl, a $C_1$-$C_6$ alkyl or any number of carbon atoms falling within these ranges. Examples of suitable straight and branched $C_1$-$C_6$ alkyl substituents include methyl, ethyl, n-propyl, 2-propyl, n-butyl, sec-butyl, t-butyl, hexyl, and the like. The group may be a terminal group or a bridging group.

"Alkenyl" as a group or part of a group denotes an aliphatic hydrocarbon group containing at least one carbon-carbon double bond and which may be straight or branched having but not limited to, at least 2 carbon atoms, 2-20 carbon atoms, 2-10 carbon atoms, 2-6 carbon atoms, or any number of carbons falling within these ranges, in the normal chain. The group may contain a plurality of double bonds in the normal chain and the orientation about each is independently E, Z, cis or trans where applicable. Exemplary alkenyl groups include, but are not limited to, ethenyl, propenyl, butenyl, pentenyl, hexenyl, heptenyl, octenyl and nonenyl. The group may be a terminal group or a bridging group.

The term "alkynyl group" as used herein includes within its meaning unsaturated aliphatic hydrocarbon groups having but not limited to, at least 2 carbon atoms or 2 to 20 carbon atoms, and having at least one triple bond anywhere in the carbon chain. Examples of alkynyl groups include but are not limited to ethynyl, 1-propynyl, 1-butynyl, 2-butynyl, 1-methyl-2-butynyl, 3-methyl-1-butynyl, 1-pentynyl, 1-hexynyl, methylpentynyl, 1-heptynyl, 2-heptynyl, 1-octynyl, 2-octynyl, 1-nonyl, 1-decynyl, and the like.

"Cycloalkyl" refers to a saturated monocyclic or fused or spiro polycyclic, carbocycle containing at least 3 carbons atoms or from 3 to 20 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. A cycloalkyl group typically is a $C_3$-$C_{20}$ alkyl group. The group may be a terminal group or a bridging group.

The term "halo" or variants such as "halide" or "halogen" as used herein refer to fluorine, chlorine, bromine and iodine.

"Haloalkyl" refers to an alkyl group as defined herein in which one or more of the hydrogen atoms has been replaced with a halogen atom selected from the group consisting of fluorine, chlorine, bromine and iodine. A haloalkyl group typically has the formula $C_nH_{(2n+1-m)}X_m$ wherein each X is independently selected from the group consisting of F, Cl, Br and I. In groups of this type n is typically from 1 to 20, from 1 to 10 or from 1 to 6. m is typically 1 to 10, 1 to 6 or 1 to 3. Examples of haloalkyl include fluoromethyl, difluoromethyl and trifluoromethyl.

The term "carbonyl" as used herein refers to a hydrocarbon that has a $R^1$—C(=O)—$R^2$ group, wherein both $R^1$ and $R^2$ may be independently a hydrogen or any of the optional substituent groups as defined above. Such carbonyls may include aldehydes or ketones.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/− 5% of the stated value, more typically +/− 4% of the stated value, more typically +/− 3% of the stated value, more typically, +/− 2% of the stated value, even more typically +/− 1% of the stated value, and even more typically +/− 0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and sub-generic groupings falling within the generic disclosure also form part of the disclosure. This includes the generic description of the embodiments with a proviso or negative limitation removing any subject matter from the genus, regardless of whether or not the excised material is specifically recited herein.

BRIEF DESCRIPTION OF FIGURES

The accompanying drawing illustrates a disclosed embodiment and serves to explain the principles of the disclosed embodiment. It is to be understood, however, that the drawing is designed for purposes of illustration only, and not as a definition of the limits of the invention.

FIG. 1 illustrates the effect of rheology modifiers in lowering the viscosity of the photocurable composition. The top diagram illustrates the photocurable composition or polymer prior to the addition of rheology modifiers, wherein non-covalent interactions between the resin molecules may be observed. The bottom diagram illustrates the photocurable composition or polymer after addition of at least one rheology modifier which may disrupt the non-covalent interactions such as hydrogen bonding interactions between hydrogen-bond acceptor or hydrogen-bond donor groups of the resin molecules.

DETAILED DESCRIPTION OF THE INVENTION

Exemplary, non-limiting embodiments of a photocurable composition will now be disclosed.

In one aspect, there is disclosed a photocurable composition which comprises 20-90% by weight of a polymerizable core resin; 20-90% by weight of a diluent resin miscible with said core resin and at least about 1% by weight of at least one rheology modifier. The rheology modifier of the composition is distinct from said diluent resin, and comprises at least one terminal functional group capable of covalently bonding to said core resin or said diluent resin or both. The terminal functional groups of the rheology modifiers are independently selected from the group consisting of acrylates, methacrylates, epoxides, oxetanes, nitriles, alkenes and alkynes. The total amount of the core resin, diluent resin and rheology modifier is about 90-100% by weight of the photocurable composition.

In another aspect, there is provided a photocurable composition comprising 20-90% by weight of a polymerizable core resin; 20-90% by weight of a diluent resin miscible with said core resin; and at least about 1% by weight of at least one rheology modifier. The rheology modifier may have a size of about 1-200 nm; and the total amount of the core resin, diluent resin and rheology modifier may be between 90 to 100% by weight of said photocurable composition.

In embodiments, the photocurable composition is a miscible liquid composition. The core resin may be miscible with the diluent resin; the core resin may be miscible with the rheology modifier; and the diluent resin may be miscible with the rheology modifier. In embodiments, the core resin, diluent resin, and rheology modifier may also be miscible with the photoinitiator and photostabilizer.

The photocurable composition may comprise the compounds or monomers disclosed herein, for example, the core resin, the diluent resin and the rheology modifier. In one embodiment, the photocurable composition may comprise a core resin, a diluent resin, a rheology modifier, a photoinitiator and a photostabilizer.

The photocurable composition described herein may have a viscosity of lower than 550 mPa·s, or lower than 500 mPa·s, or lower than 450 mPa·s, or lower than 400 mPa·s, or lower than 350 mPa·s, or lower than 300 mPa·s, or lower than 250 mPa·s, or lower than 200 mPa·s, or lower than 150 mPa·s, or lower than 100 mPa·s, or lower than 90 mPa·s, or lower than 80 mPa·s, or lower than 70 mPa·s, or lower than 60 mPa·s, or preferably lower than 50 mPa·s at 25° C. The viscosity of the photocurable composition may preferably be about 20-60 mPa·s when measured at 25° C.

In one embodiment, the photocurable composition may have a viscosity of about 32 mPa·s at 25° C. In another embodiment, the photocurable composition may have a viscosity of about 42 mPa·s at 25° C. In yet another embodiment, the photocurable composition has a viscosity of about 47 mPa·s at 25° C.

The low viscosity of the photocurable compositions disclosed herein may be attributed to the addition of at least one rheology modifier to the composition. It is postulated that the presence of rheology modifiers may aid to lower the viscosity of the composition by reducing or breaking the non-covalent interactions, for example, hydrogen bonding interactions in the photocurable composition. In embodiments, the rheology modifier may be chemically reactive with the hydrogen-bond acceptor or donor groups of the core resin or the diluent resin or both. This may disrupt non-covalent interactions, particularly hydrogen bonding interactions between discrete molecules in the composition. The rheology modifier may optionally comprise a non-reactive cyclic moiety, which may provide additional steric disruption between discrete resin molecules. This may, in turn reduce the degree of non-covalent interactions, particularly hydrogen bonding interactions in the composition.

Advantageously, the presently disclosed composition exhibits good mechanical strength upon curing. Polymers formed without the rheology modifiers disclosed herein have a Young's modulus of about 2.4 GPa, a tensile strength of about 70 MPa; and a compressive strength of about 104 MPa. The cured polymer of the photocurable resin composition disclosed herein is surprisingly able to maintain its mechanical, tensile and compressive strength; despite having a viscosity of at least 2 times lower than a composition without any rheology modifiers. Cured polymers of the photocurable composition described herein advantageously demonstrate Young's moduli of about 2.1-3.1 GPa, a tensile strength of more than 45 MPa under a load of at least 135 N and a compressive strength of more than 224 MPa.

Without being bound by theory, the mechanical strength of the composition is thought to be contributed by core resins which comprise long, stiff and inflexible carbon backbones. The core resin may comprise at least one rigid aromatic or cycloalkyl moiety in its carbon backbone which contributes to the strength of the polymer obtained from the curing of the compositions described herein.

The core resin may be a monomer which comprises at least 15 carbon atoms. The core resin monomer may comprise from 15 to 100, or from 15 to 90, or from 15 to 80, or from 15 to 70, or from 15 to 60, or from 15 to 50, or from 15 to 45, or from 15 to 40, or from 15 to 35, or from 15 to 30 carbon atoms, more preferably from 20 to 30 carbon atoms. In one embodiment, the core resin comprises 23 carbon atoms. In yet another embodiment, the core resin comprises 29 carbon atoms. Advantageously, core resins with long carbon chains lead to cured polymers with improved hardness and mechanical strength.

The core resin of the presently disclosed composition may be a monomer which comprises polymerizable terminal functional groups. The polymerizable functional groups may be functional groups which may participate in polymerization reactions such as free radical polymerization. The presence of the reactive functional groups on the core resin may enable it to form covalent linkages with other functionalized molecules in the composition. In the presently disclosed composition, the core resin may form covalent linkages with the diluent resin, or the rheology modifier, or both during the curing process. The formation of such covalent linkages may result in a polymer with an extended polymer matrix.

The terminal functional groups of the presently disclosed core resins may include methacrylates, acrylates, dienes, vinyls, alkynes, epoxides, nitriles and oxetanes. Preferable terminal functional groups of the core resin are methacrylates, acrylates and epoxides. In a preferred embodiment, the core resin of the composition may comprise methacrylate functional groups.

The core resin may comprise at least one polymerizable terminal functional group. The number of polymerizable terminal functional groups on the core resin may be between 1 to 10, between 1 to 8, between 1 to 6, between 1 to 5, between 1 to 4, between 1 to 3, more preferably, between 2 to 3 terminal functional groups. In one embodiment, the core resin comprises two polymerizable functional groups.

The core resin may be provided in an amount of about 20-90%, or about 20-85%, or about 20-80%, or about 20-75%, or about 20-70%, or about 20-65%, or about 25-65%, or about 30-65%, preferably about 35-65% by weight of the composition. In one embodiment, the core resin is provided in an amount of about 35% by weight of the photocurable composition. In another embodiment, the amount of core resin is about 65% by weight of the photocurable composition. In yet another embodiment, the core resin is provided in an amount of about 50% by weight of the composition.

The core resin used in the present composition may comprise biocompatible moieties such as bisphenol and urethane. The core resin of the composition may preferably be based on the biocompatible bisphenol framework.

Exemplary core resins include acrylate or epoxy monomers and oligomers such as bisphenol A dimethacrylate (Bis-DMA), bisphenol A diglycidyl ether methacrylate (Bis-GMA), ethoxylated bisphenol-A dimethacrylate (Bis-EMA), Tricyclo[5.2.1.02,6]decanedimethanol diacrylate, Bisphenol A glycerolate diacrylate, bisphenol A ethoxylate diacrylate, bisphenol A ethoxylate dimethacrylate (oligo), Bisphenol F ethoxylate diacylate (oligo) Bis(4-hydroxyphenyl) dimethylmethane diglycidyl ether, polyisocyanate acrylate, urethane acrylate oligomers, branched hexafunctional aliphatic urethane acrylate, DER 332, bisphenol A diglycidyl ether, bisphenol F diglycidyl ether and combinations thereof.
In embodiments, the core resin of the present photocurable composition may be; or may be composed of one or more of the following structures:
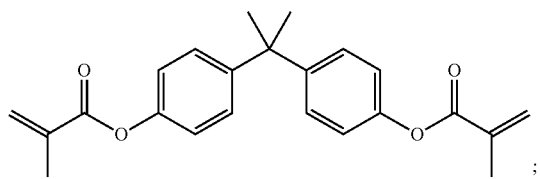
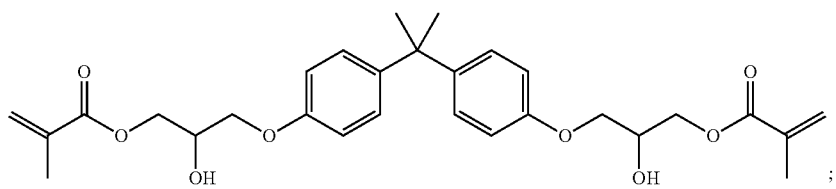
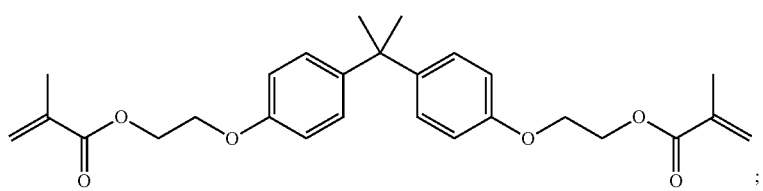
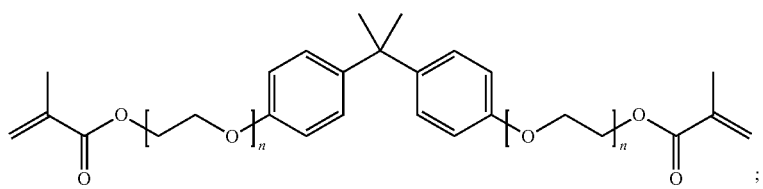
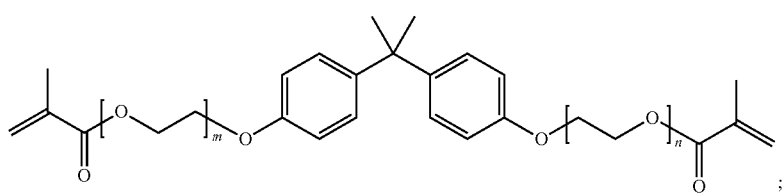
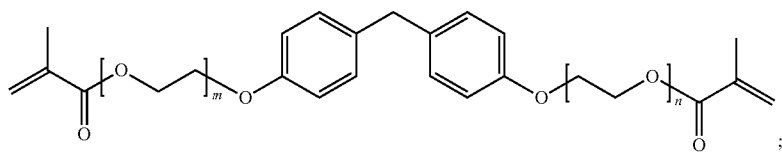
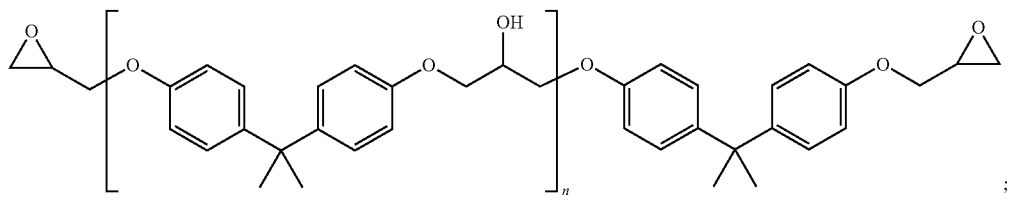
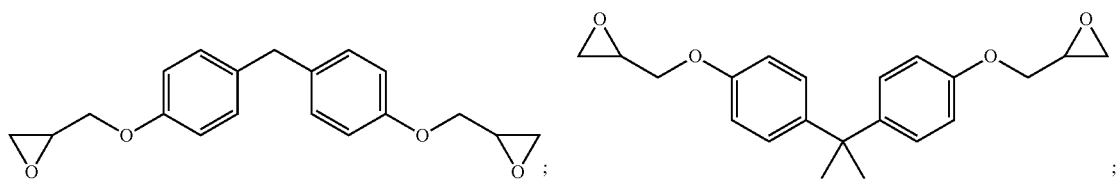

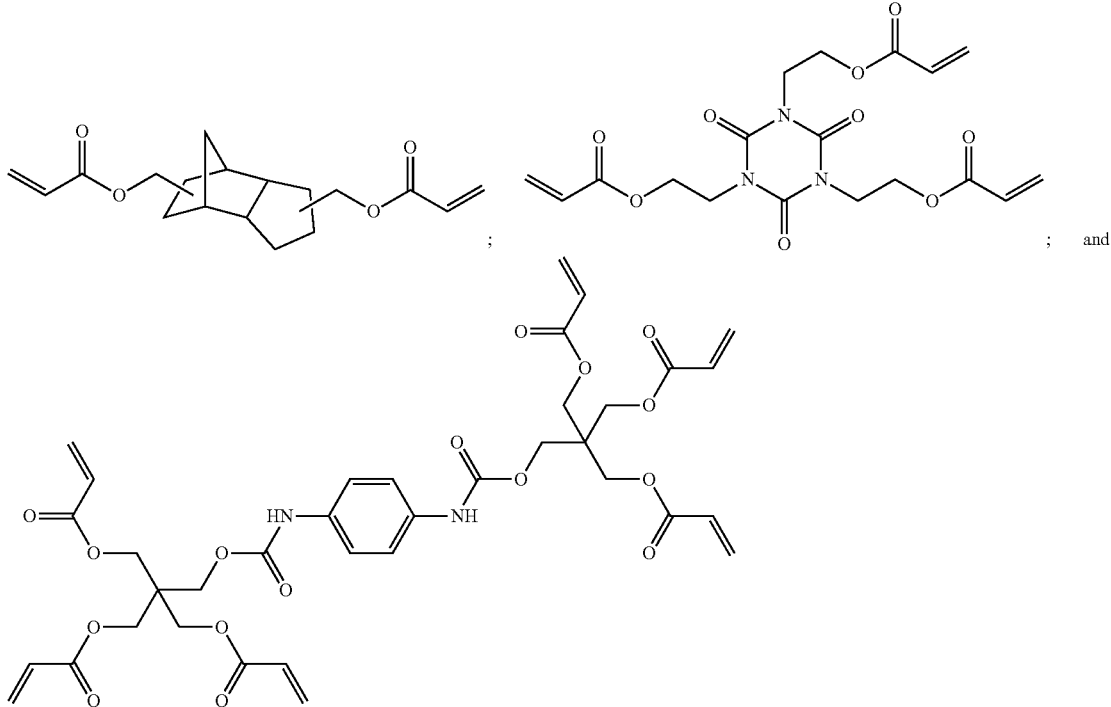

In one embodiment, the core resin comprises an acrylate or epoxy monomer of bisphenol A, e.g., bisphenol A dimethacrylate. In another embodiment, the core resin is bisphenol A diglycidyl ether methacrylate.

Neat core resins of the present photocurable composition may typically have a high viscosity of between 0.8-2.0 kPa·s at 25° C. In order to counter the high viscosity of the core resin, a diluent resin may be added to the composition.

The diluent resin may be able to reduce the viscosity of the core resin. The diluent resin may have a viscosity which is lower than the viscosity of the core resin. Accordingly, the diluent resin may be selected from neat monomers or oligomers which have a lower viscosity than the core resin. The viscosity of the diluent resin may be at least 100 times lower than the viscosity of the core resin. In one embodiment, the viscosity of the neat diluent resin may be about $2 \times 10^4$ times lower than the viscosity of the core resin.

The viscosity of the neat diluent resin may be less than 100 kPa·s, or less than 90 kPa·s, or less than 80 kPa·s, or less than 70 kPa·s, or less than 60 kPa·s, or less than 50 kPa·s, or less than 40 kPa·s, or less than 30 kPa·s, or less than 20 kPa·s, or less than 10 kPa·s, or less than 5 kPa·s, or less than 3 kPa·s, or less than 2 kPa·s, or less than 1 kPa·s, or less than 0.5 kPa·s, or less than 0.25 kPa·s, or less than 0.1 kPa·s, or less than 0.05 kPa·s, or less than 0.025 kPa·s or less than 0.01 kPa·s, or less than 5 Pa·s, or less than 2.5 Pa·s or less than 1 Pa·s, or less than 750 mPa·s, or less than 500 mPa·s, or less than 250 mPa·s, or less than 100 mPa·s, or less than 90 mPa·s, or less than 80 mPa·s, or less than 70 mPa·s, or less than 60 mPa·s, or less than 50 mPa·s, or less than 40 mPa·s, or preferably less than 30 mPa·s at 25° C.

The average molecular weight of the diluent resin may be less than 500, or less than 480, or less than 460, or less than 440, or less than 420, or less than 400, or less than 380, or less than 360, or less than 340, or less than 320, or less than 300, or less than 280, or preferably less than 260 g/mol. In one embodiment, the average molecular weight of the diluent resin is about 250 g/mol.

The diluent resin of the photocurable composition may be any resin which is miscible with the core resin. The amount of diluent resin in the presently disclosed photocurable composition is about 20-90%, or about 25-80%, or about 25-70%, or about 30-70%, or about 30-60%, or more preferably about 35-60% by weight of the composition. In one embodiment, the diluent resin is provided in an amount of about 60% by weight of the composition. In another embodiment, the diluent resin is provided in an amount of about 30% by weight of the composition. In yet another embodiment, the diluent composition is provided in an amount of about 46% by weight of the composition.

In addition, the diluent resin may comprise reactive terminal functional groups. These reactive terminal functional groups may enable the diluent resin to form one or more covalent linkages with the core resin or rheology modifier or both during the curing process. These reactive terminal functional groups may be able to participate in polymerization reactions, such as radical-initiated polymerization reactions.

The diluent resin of the present composition may comprise at least one reactive terminal functional group. The diluent resin may have one or two terminal functional groups. In one embodiment, the diluent resin comprises 2 reactive functional groups.

The terminal functional groups of the diluent resin may be independently selected from the group consisting of methacrylates, acrylates, dienes, vinyls, alkynes, epoxides, nitriles and oxetanes. Preferably, the terminal functional groups of the diluent resin may be methacrylate, acrylate and epoxide groups. In one embodiment, the diluent resin may comprise terminal methacrylate or acrylate groups.

The diluent resin may also be optionally substituted with one or more alkyl, cycloalkyl, alkenyl, cycloalkenyl, alkynyl, aromatic, hydroxyl, ether, amide or ester groups. These substituents may contribute to the miscibility of the diluent resin with the core resin. Preferably, the diluent resin may comprise alkyl, cycloalkyl, ether and amide groups. In one embodiment, the diluent resin may comprise at least one polyether group.

Examples of diluent resins may include acrylate or epoxy monomers and oligomers such as poly(ethylene glycol) diacrylate, di(ethylene glycol) diacrylate, tetra(ethylene glycol) diacrylate, 1,4-butanediol diacrylate, hydroxyl ethyl-methacrylate, 3,4-epoxy-cyclohexyl-methyl methacrylate (METHB), triethylene glycol dimethacrylate (TEGDMA), tertiobutyl cyclohexanol methacrylate, 1,6-bis[2-(methacryloyloxy)ethoxycarbonylamino]-2,4,4-trimethylhexane (UDMA), 3,3,5-trimethyl cyclohexanol methacrylate, dipentaerythritol penta-/hexa-acrylate, poly(ethylene glycol) diglycidyl ether, 1,4-butanediol diglycidyl ether, resorcinol diglycidyl ether, diglycidyl 1,2-cyclohexanedicarboxylate, poly(propylene glycol) diglycidyl ether, neopentyl glycol diglycidyl ether and combinations thereof.

Diluent resins which may be used in the presently disclosed photocurable composition disclosed herein may be one or more of the following structures:

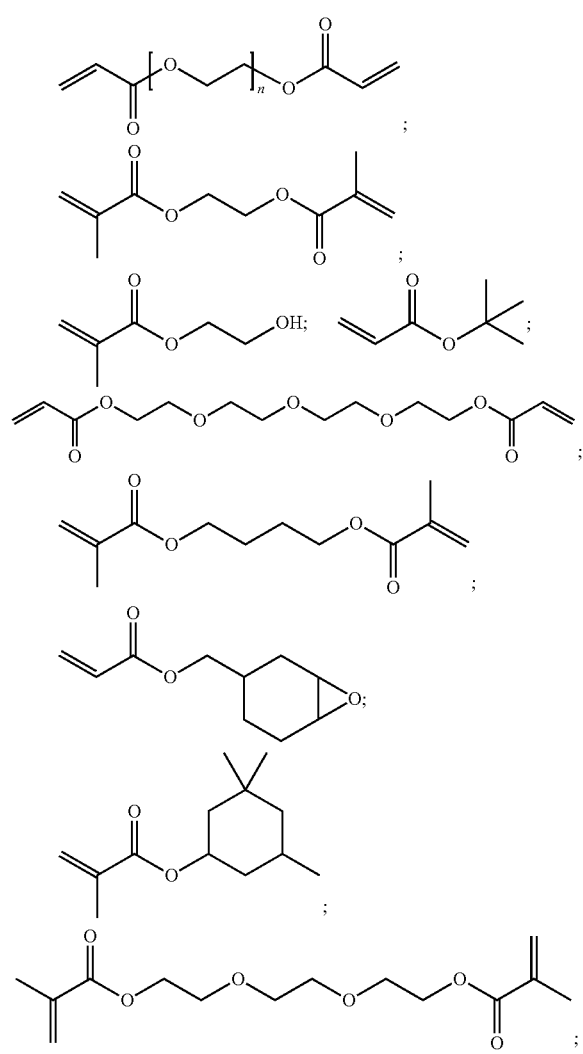

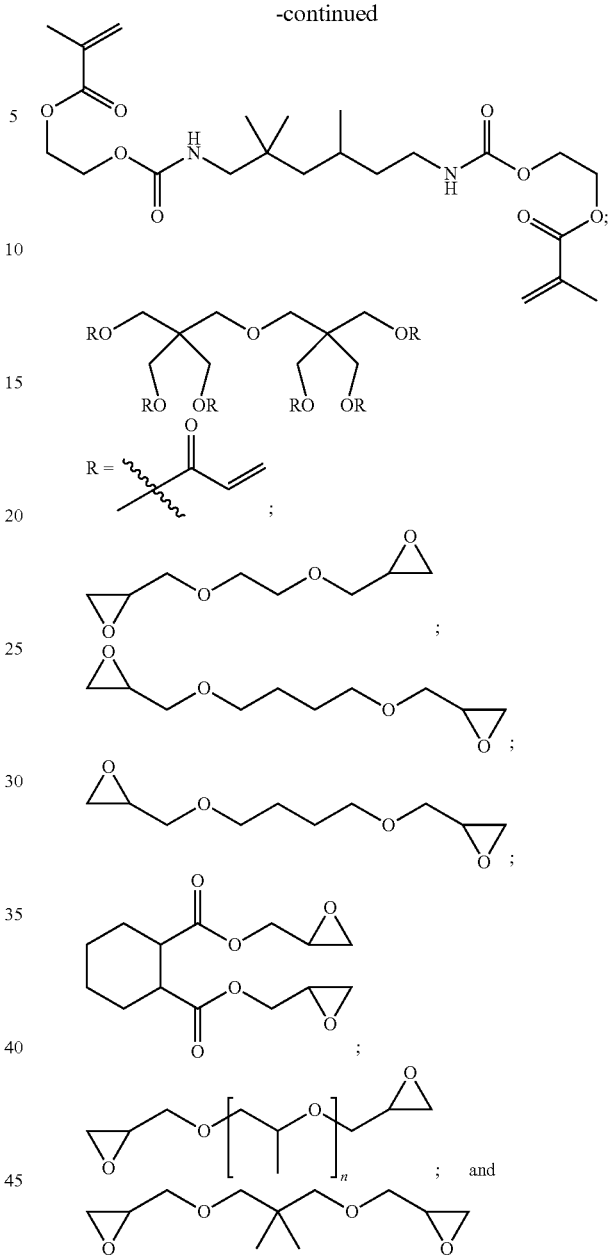

In one embodiment, the diluent resin may comprise a polyethylene glycol substituent e.g., poly(ethylene glycol) dimethacrylate.

The photocurable compositions disclosed herein may also comprise rheology modifiers. Rheology modifiers are molecules which may be able to decrease the viscosity of the composition to a desired range.

The rheology modifier may be provided in an amount of at least 1% by weight of the composition. In other embodiments, the rheology modifier may be provided in an amount of about 1-90%, or about 1-80%, or about 1-70%, or about 1-60%, or about 1-50%, or about 1-45%, or about 1-40%, or about 1-35%, or about 1-30%, or about 1-25%, or about 1-20%, or about 1-15%, or about 1-10%, or about 1-8%, or about 1-6%, or about 1-5%, or about 2-5%, or about 2-4%, or more preferably about 3-4% by weight of the composition. In one embodiment, the amount of rheology modifier in the photocurable composition described herein is less than 5% by weight of the composition. In one embodiment, the rheology modifier may be provided in an amount of about 4% by weight of the photocurable composition. In another embodiment, the rheology modifier may be provided in an amount of about 3% by weight of the photocurable composition.

The rheology modifiers may be distinct from the diluent resin. More than one rheology modifier may be provided in the same composition. Advantageously, the rheology modifier may be able to significantly decrease the viscosity of resin. Without being bound by theory, these rheology modifiers are thought to be able to increase fluidity of the photocurable composition by reducing the non-covalent interactions between the core and diluent resins and decreasing shearing forces in the composition.

Non limiting examples of non-covalent interactions which may be present in the photocurable composition include hydrogen-bonding interactions, van der Waals interactions, dipole-dipole interactions, dipole-induced dipole interactions, London dispersion forces, $\pi$-interactions and polar-t interactions.

The rheology modifiers may be able to reduce the non-covalent interactions, particularly hydrogen-bonding interactions between the long carbon chains of the core resin and the diluent resin or both. Advantageously, the reduction of hydrogen bonding interactions reduces the viscosity of the photocurable composition, without significantly reducing the mechanical strength of the resulting cured polymer.

The rheology modifiers in the presently defined photocurable composition may have at least one polar functional group, preferably at least one functional group capable of hydrogen bonding; or a spherical shape; or at least one functional group capable of hydrogen-bonding and a spherical shape. The rheology modifier may be an organic compound, a hybrid cage molecule, an inorganic oxide nanoparticle or hybrid nanoparticle.

The rheology modifier of the composition described herein may have a structure of Formula I:

$$A\text{-}P_n \qquad \text{Formula I}$$

wherein A is selected from the group consisting of optionally substituted alkyl, optionally substituted alkenyl, optionally substituted aryl group, optionally substituted alkoxy and optionally substituted organosilicon polymer;

P is optionally present, and is a polymerizable terminal functional group capable of covalently bonding to said core resin, or said diluent resin, or both; and wherein P is, in each instance, independently selected from the group consisting of acrylates, methacrylates, epoxides, oxetanes, nitriles, alkenes and alkynes; and where P is present, n is an integer of between 1 to 20.

The rheology modifier in the presently described composition comprises a central group A, which may be selected from the group consisting of optionally substituted alkyl, optionally substituted alkenyl, optionally substituted aryl group and optionally substituted organosilicon polymers. The central group A may possess a linear, dendritic or cyclic structure, preferably a cyclic structure. In embodiments, the central group may be a cyclic organic group or a cyclic organosilicon group.

In embodiments, A may be an organic group comprising 1 to 20 carbon atoms, or 1-18 carbon atoms, or 1-16 carbon atoms, or 1-14 carbon atoms, or 1-12 carbon atoms, or 1-10 carbon atoms, or 1-8 carbon atoms, or 1-6 carbon atoms, or preferably 1-5 carbon atoms. In preferred embodiments, A comprises 5 carbon atoms.

In other embodiments, A may be an organosilicon polymer having a molecular weight of about 6000, or about 100 to about 5500, or about 100 to about 5000, or about 100 to about 4500, or about 100 to about 4000, or about 100 to about 3500, or about 100 to about 3000, or about 100 to about 2500, or about 100 to about 2000, or about 200 to about 2000, or about 300 to about 2000, or about 400 to about 2000, or about 500 to about 2000, or about 600 to about 2000, or about 700 to about 2000, or about 800 to about 2000, or about 900 to about 2000, preferably about 1000 to about 2000.

The central A group may comprise at least one polar group or polar substituent which may be capable of participating in non-covalent interactions, preferably hydrogen bonding interactions. Non-limiting examples of such polar groups may include halides, ethers, amines, hydroxyls, carboxylic acids, ketones, aldehydes, esters, acrylates, methacrylates, amides, iminos, imides, siloxane, sulfhydryls and nitriles. The rheology modifiers may preferably comprise functional groups such as ethers, carboxylic acids, esters epoxides and acrylates.

Advantageously, the hydrogen bonding groups of the rheology modifier are able to interact with hydrogen acceptors/donors which are present on the carbon chain of the core resin or the diluent resin or both. Without being bound by theory, the extended intermolecular hydrogen bonding network between the hydrogen bond acceptors and donors on the alkyl chain of the core resin is thought to be one of the factors which contribute to the high viscosity of the core resin. Rheology modifiers with hydrogen bonding groups may disrupt this extended network through the formation of new short-range hydrogen bonds, which disrupts the extended hydrogen bonding network of the core resin or the diluent resin or both in the photocurable composition. The presence of these rheology modifiers may also increase the intermolecular and intramolecular distance between the hydrogen bond donor-acceptor groups on the carbon chain of the core resin and/or the diluent resin or both. This weakens the hydrogen bonding network and advantageously reduces the viscosity of the composition.

The central A group may also comprise at least one linear aliphatic or aromatic substituent comprising between 1 to 20 carbon atoms, or between 1 to 18 carbon atoms, between 1-16 carbon atoms, between 1-14 carbon atoms, between 1-12 carbon atoms, between 1-10 carbon atoms, between 1-8 carbon atoms, between 1-6 carbon atoms, between 1-4 carbon atoms, preferably 2 carbon atoms.

The presence of non-polar aliphatic and aromatic substituents on the central A group advantageously reduces the surface tension and surface energy of the rheology modifier. Without being bound by theory, the presence of such hydrophobic groups reduces non-covalent molecular interactions between the rheology modifier with the core resin or the diluent resin or both. The reduction of molecular interaction contributes to a reduction in the viscosity of the photocurable composition.

The rheology modifier of formula I may optionally comprise at least one terminal polymerizable functional group. Rheology modifiers which do not comprise polymerizable functional groups may preferably comprise functional groups and substituents which are preferably able to disrupt the hydrogen bonding network of the photocurable composition. Such rheology modifiers may preferably comprise at least one polar functional group as defined herein.

In embodiments, the rheology modifier of formula I may comprise at least one terminal polymerizable functional group, P, independently selected from the group consisting of acrylates, methacrylates, epoxides, oxetanes, nitriles, alkenes and alkynes. In embodiments, P may independently be an acrylate, methacrylate, epoxide or vinyl group. In preferred embodiments, P is a methacrylate group. These polymerizable functional groups may form a covalent bond with the core resin, or the diluent resin, or both the core and diluent resin. These functional groups may also participate in polymerization reactions such as radical polymerization reactions when exposed to suitable wavelengths of light.

Advantageously, P comprises functional groups which are capable of participating in non-covalent interactions, preferably hydrogen-bonding interactions. The presence of functional groups capable of hydrogen bonding enables the rheology modifier to interact with other hydrogen bonding groups on the core resin, diluent resin or other rheology modifiers. This interaction advantageously disrupts the extended hydrogen bonding network in the composition and leads to lower viscosity of the photocurable composition.

Polymerizable group P may be covalently linked to the central A group via a linker B, represented by Formula I(a) below.

  Formula I(a)

B may be an aliphatic or aromatic group. B may be a branched or linear linker group, preferably a straight chain aliphatic or aromatic group. B may comprise 1 to 10 carbon atoms, or about 1 to 8 carbon atoms, or about 1 to 6 carbon atoms, or about 1 to 5 carbon atoms, or about 1 to 4 carbon atoms, or preferably about 1 to 3 carbon atoms. In embodiments, B comprises 1 carbon atom or 3 carbon atoms.

In each instance, B may be independently selected from the group consisting of: optionally substituted alkyl, optionally substituted alkenyl, optionally substituted aryl, optionally substituted arylalkyl, optionally substituted arylalkenyl, optionally substituted alkylaryl, optionally substituted alkenylaryl, optionally substituted alkoxy, optionally substituted alkenyloxy, optionally substituted aryloxy and optionally substituted siloxy groups. B may preferably be an optionally substituted alkyl group, an optionally substituted aryl group, an optionally substituted alkoxy group, an optionally substituted aryloxy group, an optionally substituted siloxy group. preferably an aliphatic alkyl group. In preferred embodiments, B is a aliphatic alkyl group or an aliphatic alkoxy group.

The presence of linker groups on the rheology modifier may contribute to an increase in the size of the rheology modifier. Advantageously, rheology modifiers with increased sizes may be able to increase the distance between the alkyl chains of the core resin and the diluent resin. The increase in intramolecular and intermolecular distance of the alkyl chains in the composition reduces the non-covalent interactions, particularly the hydrogen bonding interactions between the alkyl chains of the core resin and the diluent resin or both.

The rheology modifiers of formula I may comprise more than one terminal polymerizable group P. The number of acrylate groups on the rheology modifiers may be determined by the number n.

In the rheology modifier of Formula I, n may be an integer of between 1 to 20, between 1 to 18, between 1 to 16, between 1 to 14, between 1 to 12, or preferably between 1 to 10. In embodiments, n is 1, indicating the presence of a single polymerizable functional group in the molecule. In other embodiments, n is 8, indicating that the rheology modifier comprises 8 polymerizable functional groups.

In embodiments, the rheology modifier may comprise at least 3 terminal polymerizable functional groups P. Advantageously, compositions which comprise rheology modifiers with at least 3 terminal polymerizable functional groups may enable fast curing of the resin composition. The curing time of compositions which comprise at least 3 terminal polymerizable functional groups may be about 50 to 200 times faster than compositions without non-acrylate rheology modifiers.

In one embodiment, the rheology modifier may be a spherical polyoctahedral silsesquioxane (POSS) with 8 terminal acrylate groups branching from the silicon atoms. Advantageously, the acrylate-substituted POSS cage modifiers are able to reduce the viscosity of the photocurable composition by almost three times, as compared to photocurable compositions with do not comprise the rheology modifier. Surprisingly, the cured polymer demonstrates increased mechanical strength as well although the viscosity of the composition is almost three times lower.

This may be attributed to the rheology modifier which comprises a spherical central core structure and 8 terminal acrylate groups. The terminal acrylate groups and the spherical central core may act synergistically to disrupt the hydrogen bonding network of the core resin and/or the diluent resin. This significantly reduces the viscosity of the photocurable composition, without affecting or compromising the mechanical strength of the cured polymer. Such compositions are suitable for use in 3-dimensional printing of a desired structure.

Advantageously, compositions which comprise rheology modifiers with one or more terminal functional group may result in cured polymers with low viscosity and improved mechanical strength. The presence of at least one terminal functional group may allow the rheology modifier to form at least one covalent linkage with the core resin, or the diluent resin, or both upon curing. The incorporation of the rheology modifier in the polymer matrix advantageously interrupts the non-covalent interactions between the components of the liquid photocurable composition and increases the degree of polymerization in the cured polymer which may contribute to its increased mechanical strength. This results in a composition of low viscosity in the liquid state, and a polymer with increased mechanical strength upon curing.

The rheology modifiers of the photocurable composition described herein may also be substantially spherical. Rheology modifiers which are substantially spherical may have an outer surface or perimeter on which every point may be substantially equidistant from the center of the structure. In some embodiments, the spherical rheology modifier may be organic hyperbranched molecules, hybrid cage molecules, inorganic oxide nanoparticles or hybrid nanoparticles.

Advantageously, these spherical rheology modifiers may be able to reduce the non-covalent interactions in the composition. The homogenous dispersion of such spherical rheology modifiers in the composition may be able to increase the distance between the long carbon chains of the core resin and the diluent resin or both. This increased distance weakens non-covalent interactions in the photocurable composition. Non-limiting examples of such non-covalent interactions include hydrogen bonding, van der Waals interactions, dipole-dipole interactions, π-interactions and polar-t interactions.

Surprisingly, cured polymers obtained from photocurable compositions comprising spherical rheology modifiers demonstrate good mechanical strength. It is thought that the homogenous dispersion of these rheology modifiers described herein between in the core and diluent resin allows the polymer to resist shearing or compressive forces which are applied to the cured polymer composition.

Spherical branched rheology modifiers may comprise a spherical core structure as well. The spherical central core structure may be a spherical inorganic or hybrid cage molecule. The spherical rheology modifier may be a metal-organic framework or a polyhedral oligomeric silsesquioxane (POSS) molecule. In one embodiment, the spherical rheology modifier is a functionalized POSS cage molecule. In one embodiment, the branched rheology modifier is a POSS molecule comprising 8 branching units.

Advantageously, branched rheology modifiers based on a spherical core structure may interrupt the hydrogen bonding network of the core resin and/or diluent resin. The branched rheology modifiers may be uniformly distributed in the composition. Without being bound by theory, it is thought that the branched rheology modifier may increase the distance between the alkyl chains of the core resin. The increased distance may lead to weakened hydrogen bonding of the core resin, which results in photocurable compositions with low viscosity.

Examples of rheology modifiers may include tetrahydrofurfuryl methacrylate, 2-carboxyethyl acrylate, trimethylolpropane triacrylate, pentaerythritol triacrylate, di(trimethylolproane) tetraacrylate, pentaerythritol tetraacrylate, 2-{[(butylamino)carbonyl]oxy}ethyl acrylate, vinyl T-structure polymers, methacryloxypropyl T-structure siloxanes, methacryl POSS cage mixture, methacrylethyl POSS, trimethylolpropane triglycidyl ether, tris-(4-hydroxyphenyl)methane triglycidyl ether, monophenyl functional tris(epoxy terminated polydimethylsiloxane), epoxycyclohexyl POSS cage mixture, triglycidylisobutyl POSS and glycidyl POSS cage.

In embodiments, the rheology modifiers may be selected from one or more compounds disclosed below:

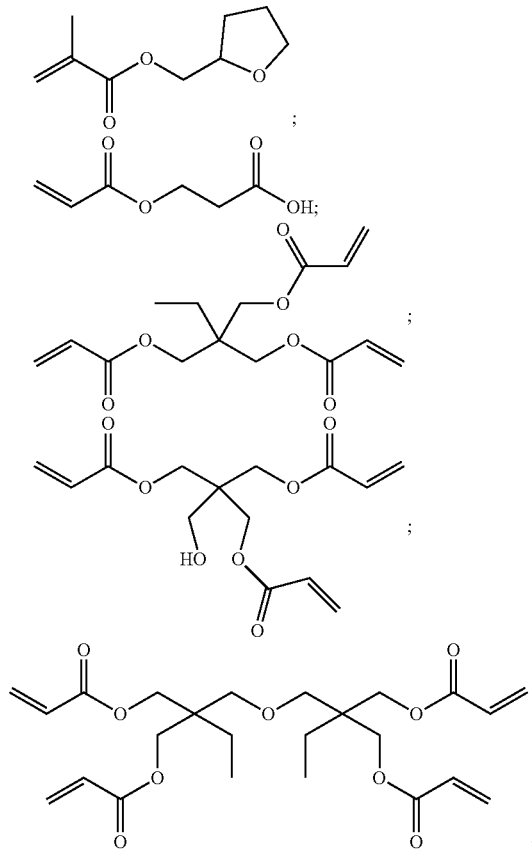

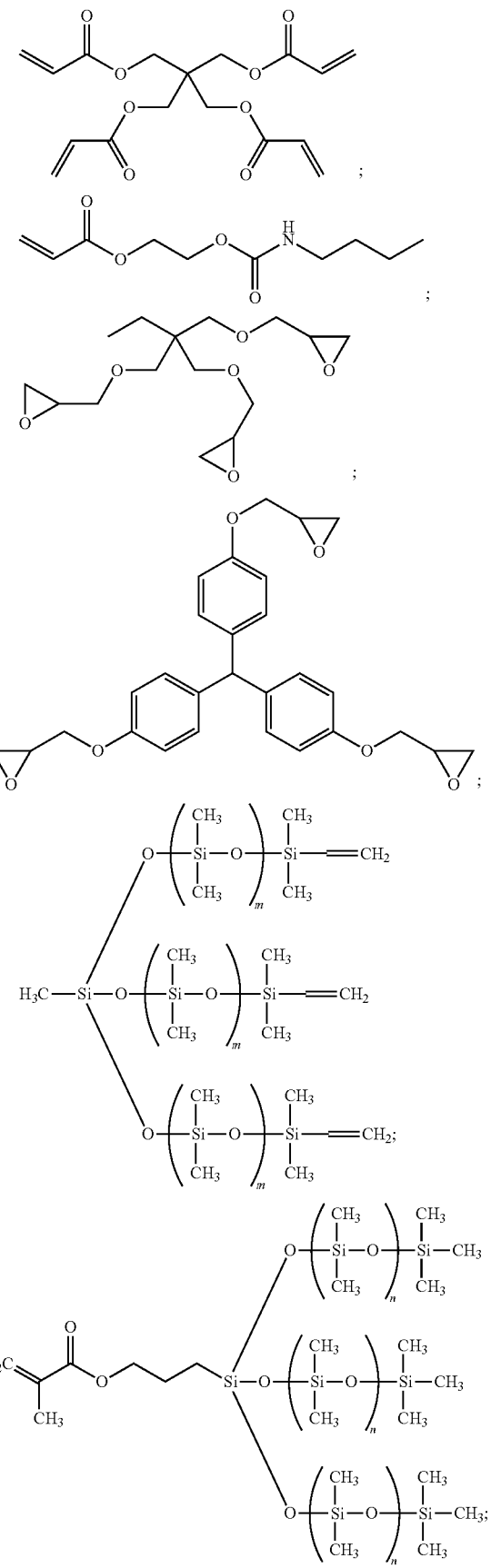

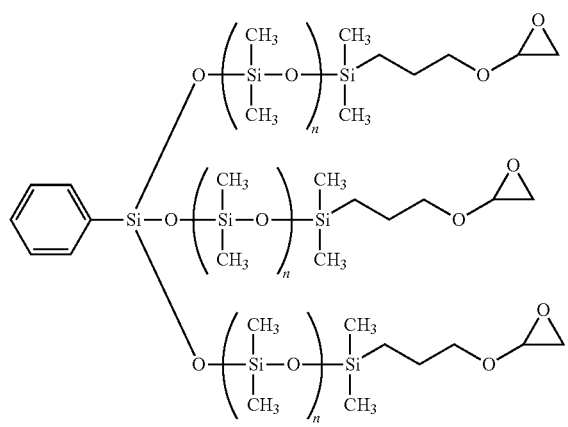

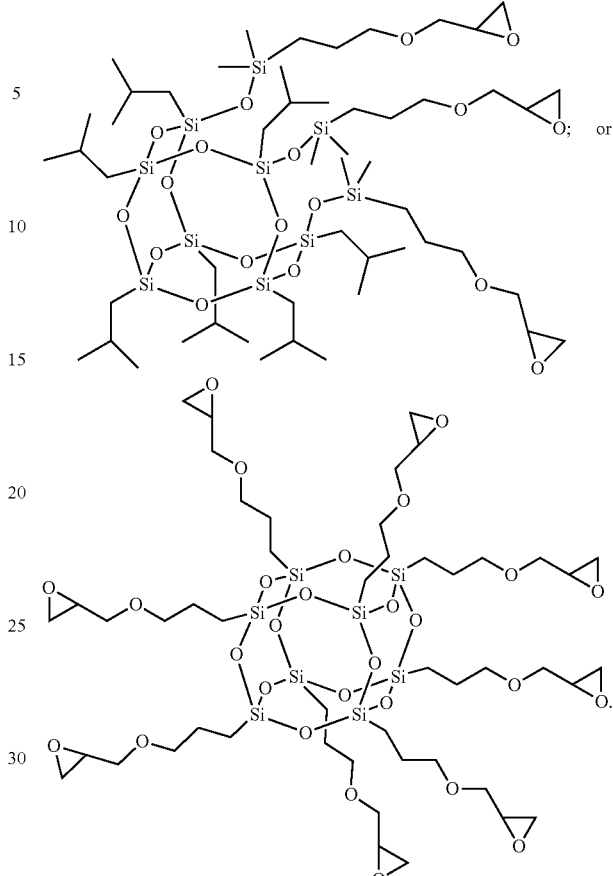

In embodiments, the rheology modifier of the photocurable composition described herein is spherical. Such rheology modifiers may be nanoparticles or hybrid cage molecules. The nanoparticles may be inorganic oxide nanoparticles and hybrid nanoparticles. The nanoparticles may preferably be spherical in shape. Advantageously, spherical nanoparticles of a defined diameter are able to disrupt the non-covalent interactions, for example hydrogen-bonding interactions, between the core resin and/or the diluent resin.

Without being bound by theory, the spherical nanoparticles disclosed herein may be uniformly interspersed between the chains of the core resin and/or the diluent resin. The uniform dispersion of nanoparticles may increase the distance between the carbon chains of the core resin or the diluent resin or both the core resin and the diluent resin, which may weaken the non-covalent interactions of the core resin and/or the diluent resin. This disruption in non-covalent interactions may result in photocurable compositions with lower viscosity.

The nanoparticles may have a particle size/diameter of about 1-200 nm, or about 1-180 nm, or about 1-160 nm, or about 1-140 nm, or about 1-120 nm, or about 1-100 nm, or about 1-80 nm, or about 1-60 nm, or about 1-50 nm, or about 1-40 nm, or about 1-30 nm, more preferably about 1-20 nm. The nanoparticles may be of a regular or irregular shape. Regular shaped particles may be spherical, cylindrical, oblong or ellipse. Where the nanoparticles are not spherical in shape, the above disclosed particle size shall apply to its equivalent spherical diameter. These rheology modifiers may not form covalent linkages with the core resin or the diluent resin or both.

In embodiments, such spherical rheology modifiers may also include hybrid cage molecules such as polyhedral oligomeric silsequioxanes cage molecules (POSS). The POSS molecules may be optionally substituted with alkyl, cycloalkyl, aromatic, haloalkyl, and polyether groups.

In some embodiments, rheology modifiers which may not form covalent linkages with the polymer matrix may be hybrid cage molecules. Such rheology modifiers are homogenously distributed in the composition. Such hybrid cage molecules may include PEG POSS, trifluoropropyl POSS, octamethyl POSS and octaphenyl POSS.

In embodiments, the POSS rheology modifiers may be one of the following:

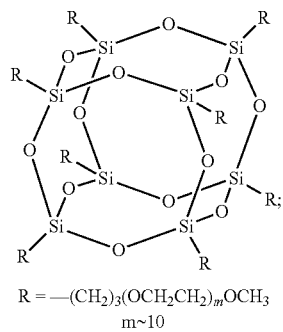

$R = -(CH_2)_3(OCH_2CH_2)_mOCH_3$
m~10

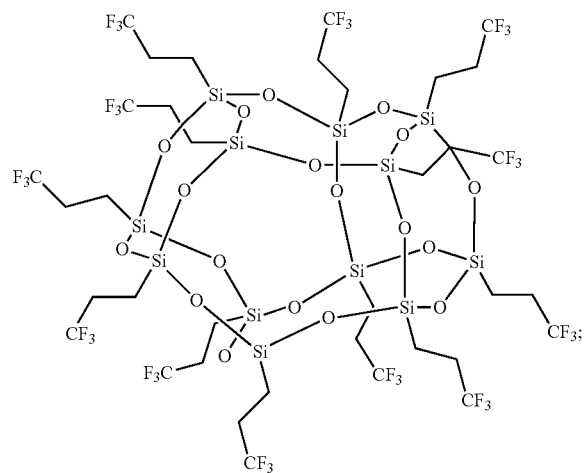

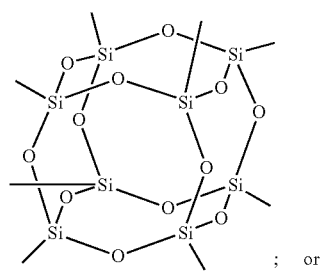
; or

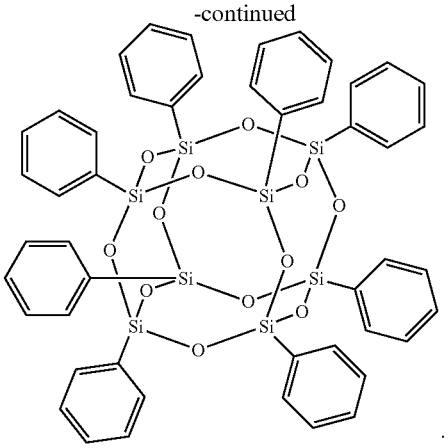

In embodiments, the sperical rheology modifiers may comprise a plurality of polar groups or substituents on its surface. Polar groups and substituents may include electronegative atoms such as oxygen, nitrogen and halogens. The polar groups of the rheology modifiers may include acrylates, methacrylate, epoxide, aldehyde, ketone, esters, carbonyls, carboxylic acids, amines, amides, ethers, nitriles, hydroxyls, thioethers and halides. The polar groups on the rheology modifier may preferably be halide, hydroxyl, carboxylic acid, ether or amine groups. In embodiments, the polar group on the modifier may preferably be carboxylic acid, ethers or amines.

Advantageously, the inclusion of rheology modifiers with polar substituents may result in photocurable compositions of low viscosity. The rheology modifiers with polar substituents may aid to disrupt the hydrogen-bonding network between the polar groups on the core resin and/diluent resin. The disruption of the hydrogen bonding on the core resin and/or the diluent resin may result in compositions which have lower viscosity. Advantageously, photocurable compositions which comprise the rheology modifier may maintain its mechanical strength despite the lower viscosity.

The polar groups on the rheology modifier may preferably be able to participate in hydrogen bonding. In some embodiments, the rheology may preferably be substituted with at least one functional group which may be a hydrogen bond acceptor. Functional groups which may be hydrogen bond acceptors may be ethers, tertiary amine, aldehyde, ketone, nitrile, thioether, halogen or esters. The hydrogen bond acceptor may preferably be ethers or halogens.

In embodiment, the rheology modifier may be inorganic oxide nanoparticles. The nanoparticle rheology modifiers may be any metalloid oxide or metal oxide nanoparticle. Non-limiting examples of inorganic oxide nanoparticle rheology modifiers may include aluminum oxide, silicon oxide, silver oxide, titanium oxide, zinc oxide, iron oxide, cerium oxide, tin oxide, zirconium oxide or copper oxide nanoparticles. The nanoparticle rheology modifier may preferably be silicon oxide, titanium oxide or zinc oxide nanoparticles.

In embodiments, the photocurable composition further comprises at least one photoinitiator and at least one photostabilizer. The amount of photoinitiator and photostabilizer may be no more than about 5% by weight of the photocurable composition. The total amount of the core resin, diluent resin, rheology modifier, photoinitiator and photostabilizer may be 100% by weight of the photocurable composition.

Photoinitiators which may be used in the composition described herein include compounds which may absorb visible or ultraviolet light to generate reactive species such as free radicals. When contacted with reactive functional groups, these reactive species may be able to initiate a polymerization reaction. For example, the free radical species generated from the photoinitiator are able to react with the reactive functional groups of the core resin, the diluent resin, or the rheology modifier; thereby initiating a radical polymerization chain reaction.

The photoinitiators may be provided in an amount of at least 0.5% by weight of the composition, or from 0.5%-5%, or from 0.5-4.5%, or from 0.5-4.0%, or from 0.5-3.5%, or from 0.5-3.0%, or from 0.5-2.5%, or from 0.5-2.0%, or from 0.5-1.5%, or more preferably from 0.5-1% by weight of the composition. In one embodiment, the photoinitiator is provided in an amount of 0.8% by weight of the composition.

The photoinitiators may be selected according to the emission range of the ultraviolet or visible light source. The photoinitiators may have light or ultraviolet absorption bands which overlap with the emission spectrum of the ultraviolet or visible light source used for curing the present photocurable composition. The photoinitiators may also have light or ultraviolet absorption bands which are distinct from the absorption bands of the core resin, diluent resin and rheology modifier.

Examples of ultraviolet and visible light photoinitiators may include bis(2,4,6-trimethyl benzol)phenylphosphine oxide (IRGACURE 819), Phenylbis(2,4,6-trimethylbenzol) phosphine oxide (BAPO), 2,4,6-trimethylbenzoly diphenyl phosphine (TPO), 2-hydroxy-2-methyl-1-phenyl-1-propane (DAROCUR 1173) and benzophenone. In one embodiment, the photoinitiator is phenylbis(2,4,6-trimethylbenzol)phosphine oxide.

Optionally, the photocurable composition may also comprise photostabilizers. Photostabilizers may be molecules which are able to reduce the degradation of polymers caused by exposure to ultraviolet radiation. The photoprotective effects may be due to the reflection or absorption of radiation by the photostabilizers. Photostabilizers which absorb UV radiation are also known as photoabsorbers.

Photostabilizers may also be able to control the curing process of the composition. When used in 3-D printing, the photostabilizers in the photocurable composition advantageously allows more accurate printing of the desired polymeric structures.

The photostabilizers may be added in an amount of at least 0.01% by weight of the composition, or about 0.01-0.5%, or about 0.01-0.45%, or about 0.01-0.40%, or about 0.01-0.35%, or about 0.01-0.30%, or about 0.01-0.25%, more preferably about 0.05-0.25% by weight of the photocurable composition. In one embodiment, the amount of photostabilizer is 0.2% by weight of the photocurable composition.

In some embodiments, the composition comprises photoabsorbers. Examples of photoabsorbers may include Sudan I-IV, 2,5-Bis(5-tert-butyl-benzoxazol-2-yl)thiophene, 4-methoxyphenol and butylated hydroxytoluene, as well as photoabsorbers well known in the art.

The presently disclosed photocurable composition may be a homogenous composition. The components of the photocurable composition, for example, the core resin, the diluent resin and the rheology modifier may be miscible with each other and may be homogenously distributed and dispersed throughout the composition. The core resin may be miscible with the diluent resin; the core resin may be miscible with the rheology modifier; and the diluent resin may be miscible with the rheology modifier. In embodiments, the core resin, diluent resin, and rheology modifier may also be miscible with the photoinitiator and photostabilizer.

In embodiments, the photocurable composition is a neat resin composition. The photocurable composition may be substantially free from fillers, reinforcements and pigments which may interfere or obscure absorption of radiation from the visible light or ultraviolet source. The photocurable composition may also be substantially free from fillers and materials which may cause volumetric shrinkage.

Advantageously, the neat photocurable composition may be polymerized within about 5 seconds of exposure to a light or ultraviolet source. In one embodiment, the composition is cured within about 5.8 seconds of exposure to an ultraviolet source. This may be attributed to the presence of one or more reactive functional groups, for example, 2 functional groups, on each component of the composition, which may enable rapid polymerization to take place.

Also advantageously, the absence of fillers, reinforcements and pigments in the neat photocurable composition described herein may allow efficient absorption of radiation from the light source. This may enable the rapid polymerization of the core resin, diluent resin and rheology modifier to take place within at least 5 seconds of exposure to the ultraviolet light source.

EXAMPLES

Non-limiting examples of the invention will be further described in greater detail by reference to specific Examples, which should not be construed as in any way limiting the scope of the invention.

The photocurable compositions exemplified herein were prepared according to the general formulation below:

TABLE 1

General components of the photocurable compositions

| Components | Percentage (wt %) |
|---|---|
| Core Resin | 20-90 |
| Diluent Resin | 20-90 |
| Rheology Modifier | At least 1% |
| Photoinitiator | 0.1-5 |
| Photostabilizer | 0-0.2 |

Example 1

Preparation and Measurement of Example Composition 1

All components listed in Table 2 were weighed into a flask and stirred in the absence of light for 8-24 hours until all solid contents were dissolved and homogeneous. The measured viscosity at 25° C. was about 32 mPa·s.

To evaluate their printability and mechanical strength, dog-shape tensile bars were printed on a DLP printer [Little RP with build volume 60 mm(X) 40 mm(Y) 100 mm(Z), which uses DLP projector with a resolution of 1024×768 (Brand & model: Acer P128) as light source and Creation Workshop as controlling software.] Printing was carried out with slice thickness of 50 μm. Exposure time per layer was 5800 ms. After printing, the printed bar was washed thoroughly with iso-propanol, air dried and placed inside a UV oven for further curing.

The compressive strength was measured on the Instron 4500 testing system by upgrading the control system with Instron's advanced 5500 electronics and software.

TABLE 2

Example Composition 1

| Components | Percentage (wt %) |
| --- | --- |
| Bisphenol A dimethacrylate | 35 |
| Poly(ethylene glycol) diacrylate | 60 |
| Tetrahydrofurfuryl methacrylate | 4 |
| Phenylbis(2,4,6-trimethylbenzoyl)phosphine oxide | 0.8 |
| 2,5-Bis(5-tert-butyl-benzoxazol-2-yl)thiophene | 0.2 |

Example 2

Preparation and Measurement of Example Composition 2

All components listed in Table 3 were weighed into a flask and stirred in the absence of light for 8-24 hours until all solid contents were dissolved and homogeneous. The measured viscosity at 25° C. was about 42 mPa·s.

To evaluate their printability and mechanical strength, dog-shape tensile bars were printed on a DLP printer [Little RP with build volume 60 mm(X) 40 mm(Y) 100 mm(Z), which uses DLP projector with a resolution of 1024×768 (Brand & model: Acer P128) as light source and Creation Workshop as controlling software.] Printing was carried out with slice thickness of 50 μm. Exposure time per layer was 5800 ms. After printing, the printed bar was washed thoroughly with iso-propanol, air dried and placed inside a UV oven for further curing.

TABLE 3

Example Composition 2

| Components | Percentage (wt %) |
| --- | --- |
| Bisphenol A dimethacrylate | 35 |
| Poly(ethylene glycol) diacrylate | 60 |
| Tetrahydrofurfuryl methacrylate | 4 |
| Phenylbis(2,4,6-trimethylbenzoyl)phosphine oxide | 0.8 |
| 2,5-Bis(5-tert-butyl-benzoxazol-2-yl)thiophene | 0.2 |

Example 3

Preparation and Measurement of Example Composition 3

All components listed in Table 4 were weighed into a flask and stirred in the absence of light for 8-24 hours until all solid contents were dissolved and homogeneous. The measured viscosity at 25° C. was about 47 mPa·s.

To evaluate their printability and mechanical strength, dog-shape tensile bars were printed on a DLP printer [Little RP with build volume 60 mm(X) 40 mm(Y) 100 mm(Z), which uses DLP projector with a resolution of 1024×768 (Brand & model: Acer P128) as light source and Creation Workshop as controlling software.] Printing was carried out with slice thickness of 50 μm. Exposure time per layer was 5800 ms. After printing, the printed bar was washed thoroughly with iso-propanol, air dried and placed inside UV oven for further curing.

TABLE 4

Example Composition 3

| Components | Percentage (wt %) |
| --- | --- |
| Bisphenol A diglycidyl ether methacrylate | 50 |
| Poly(ethylene glycol) diacrylate | 46 |
| Methacryl POSS Cage Mixture | 3 |
| Phenylbis(2,4,6-trimethylbenzoyl)phosphine oxide | 0.8 |
| 2,5-Bis(5-tert-butyl-benzoxazol-2-yl)thiophene | 0.2 |

Example 4

Preparation and Measurement of Example Composition 4

All components listed in Table Y were weighed into a flask and stirred in the absence of light for 8-24 hours until all solid contents were dissolved and homogeneous. The measured viscosity at 25° C. was about 52 mPa·s.

To evaluate their printability and mechanical strength, dog-shape tensile bars were printed on a DLP printer [Little RP with build volume 60 mm(X) 40 mm(Y) 100 mm(Z), which uses DLP projector with a resolution of 1024×768 (Brand & model: Acer P128) as light source and Creation Workshop as controlling software.] Printing was carried out with slice thickness of 50 μm. Exposure time per layer was 5800 ms. After printing, the printed bar was washed thoroughly with iso-propanol, air dried and placed inside a UV oven for further curing.

TABLE 5

Example Composition 4

| Components | Percentage (wt %) |
| --- | --- |
| Bisphenol A diglycidyl ether methacrylate | 50 |
| Poly(ethylene glycol) diacrylate | 45 |
| PEG POSS cage | 4 |
| Phenylbis(2,4,6-trimethylbenzoyl)phosphine oxide | 0.8 |
| 2,5-Bis(5-tert-butyl-benzoxazol-2-yl)thiophene | 0.2 |

Example 5

Comparison of Mechanical Strength

The Young's modulus was measured on a universal tensile machine ASTM D638-03. At least five printed samples for each resin were tested by INSTRON universal testing machine, with a loading rate of 1 mm/s. Results are an average of measurements obtained from at least five specimens.

The compressive strength was measured on the Instron 4500 testing system by upgrading the control system with Instron's advance 5500 electronics and software. It was measured using a 50 kN load cell set to run at 2,000 pounds with crosshead speed at 2 inches (50.8 mm) per minute. Compressive strength was tested using cylindrical specimens (1 cm diameter, 4 cm height) prepared on a DLP printer and washed with OPA, then cured in the UV oven for 30 min and further cured in an oven at 100° C. for 2 hours.

TABLE 6

Comparison of Mechanical Strength

| Composition | Young's Modulus (MPa) | Maximum Tensile stress (MPa) | Load at Maximum Tensile stress (N) | Compressive strength (MPa) |
|---|---|---|---|---|
| Example Composition 1 | 2430.45 ± 110 | 45.85 ± 0.65 | 138.21 ± 2.2 | 244.78 ± 21.4 |
| Example Composition 2 | 2749.55 ± 125 | 46.23 ± 4.67 | 148.02 ± 15 | 259.70 ± 25.6 |
| Example Composition 3 | 2835.69 ± 105 | 192.37 ± 0.05 | 192.37 ± 2.1 | 318.16 ± 18.9 |
| Example Composition 4 | 2695.44 ± 105 | 57.13 ± 0.45 | 554.35 ± 3.1 | 286.47 ± 32.1 |

Example 6

Preparation of Comparative Compositions

Comparative Compositions were prepared using the same method of preparing Example Composition, without the addition of rheology modifier.

Comparative Composition 1 was prepared using the components listed in Table 2 except tetrahydrofurfuryl methacrylate.

Comparative Composition 2 was prepared using the components listed in Table 3 except tetrahydrofurfuryl methacrylate.

Comparative Composition 3 was prepared using the components listed in Table 4 or Table 5 except methacryl POSS Cage Mixture and PEG POSS Cage.

TABLE 7

Comparison of Viscosity (at 25° C.)

| Composition | Viscosity at 25° C. (mPa · s) |
|---|---|
| Example Composition 1 | 32 |
| Example Composition 2 | 42 |
| Example Composition 3 | 47 |
| Example Composition 4 | 52 |
| Comparative Composition 1 | 89 |
| Comparative Composition 2 | 89 |
| Comparative Composition 3 | 137 |

INDUSTRIAL APPLICABILITY

The photocurable composition disclosed herein may be used for 3D printing of dental structures. For example, the composition may be used in liquid-based 3D printing techniques such as SLA or DLP to print various dental structures, such as implants, surgical guides, braces, dentures, crowns and bridges. In addition, the photocurable composition may also be used for bone tissue scaffold printing.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A photocurable composition consisting of:
   i) 20% by weight to 55% by weight of a polymerizable core resin having 20 carbon atoms to 40 carbon atoms;
   ii) 40% by weight to 70% by weight of a diluent resin miscible with said core resin, having up to two reactive terminal functional groups capable of covalently bonding to said core resin, or rheology modifier, or both; wherein the diluent resin has a viscosity of less than 1 Pa·s
   iii) at least about 1% by weight of at least one rheology modifier, said rheology modifier being distinct from said diluent resin;
   iv) photoinitiators; and
   v) photostabilizers
   wherein the rheology modifier is selected from:
   (a) a compound of general formula I:

$$A\text{-}P_n \quad \text{Formula I}$$

wherein A is a polyhedral oligomeric silsequioxanes cage (POSS);
   P is a polymerizable terminal functional group capable of covalently bonding to said core resin, or said diluent resin, or both; and wherein P is, in each instance, independently selected from the group consisting of acrylates, methacrylates, and epoxides, optionally the polymerization terminal functional group P is linked to A via a linker group B, where B is present, B is absent of Si, and wherein n is an integer of 1 to 20; or
   (b) a hybrid cage molecule that does not form covalent linkages with any of the components i) and ii).

2. The photocurable composition of claim 1, wherein P is an acrylate group.

3. The photocurable composition of claim 1, wherein the polymerization terminal functional group P is linked to A via a linker group B, wherein the linker group B is selected from the group consisting of optionally substituted alkyl, optionally substituted alkenyl, optionally substituted aryl, optionally substituted arylalkyl, optionally substituted arylalkenyl, optionally substituted alkylaryl, optionally substituted alkenylaryl, optionally substituted alkoxy, optionally substituted alkenyloxy, and optionally substituted aryloxy.

4. The photocurable composition of claim 1, wherein the rheology modifier is a methacrylate functionalized POSS cage molecule:

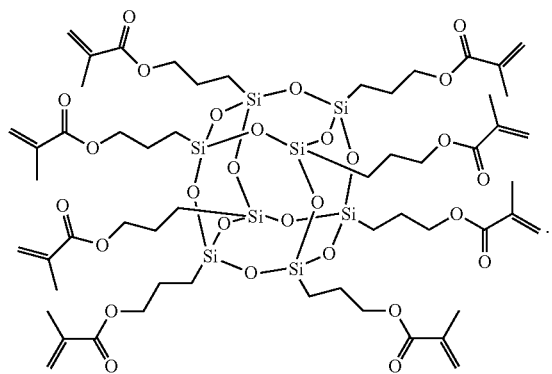 [SMILES: C=C(C)C(=O)OCCC[Si]12O[Si]3(CCCOC(=O)C(=C)C)O[Si]4(CCCOC(=O)C(=C)C)O[Si](CCCOC(=O)C(=C)C)(O1)O[Si]1(CCCOC(=O)C(=C)C)O[Si](CCCOC(=O)C(=C)C)(O2)O[Si](CCCOC(=O)C(=C)C)(O3)O[Si](CCCOC(=O)C(=C)C)(O4)O1]

5. The photocurable composition of claim 1, wherein the rheology modifier is present in an amount of about 1% by weight to 50% by weight of the photocurable composition.

6. The photocurable composition of claim 1, wherein the rheology modifier is present in an amount of 1% by weight to 10% by weight of the photocurable composition.

7. The photocurable composition of claim 1, wherein the polymerizable core resin is present in an amount of 35% by weight to 50% by weight of the photocurable composition.

8. The photocurable composition of claim 1, wherein the diluent resin is present in an amount of about 45% by weight to 60% by weight of the photocurable composition.

9. The photocurable composition of claim 1, wherein the hybrid cage molecule of (b) is selected from the group consisting of metal-organic framework, organosilicon hybrid cage molecules and combinations thereof.

10. The photocurable composition of claim 9, wherein hybrid cage molecule of (b) is an optionally substituted organosilicon hybrid cage molecule.

11. The photocurable composition of claim 10, wherein hybrid cage molecule of (b) is an optionally substituted polyhedral oligomeric silsequioxane (POSS) cage.

12. The photocurable composition of claim 11, wherein the POSS cage is substituted with alkyl, cycloalkyl, haloalkyl, aromatic and polyether groups.

13. The photocurable composition of claim 12, wherein the POSS cage is selected from the group consisting of polyethylene glycol POSS, trifluoropropyl POSS, octamethyl POSS, octaphenyl POSS and combinations thereof.

* * * * *

UNITED STATES PATENT AND TRADEMARK OFFICE
CERTIFICATE OF CORRECTION

PATENT NO. : 12,258,449 B2
APPLICATION NO. : 17/610738
DATED : March 25, 2025
INVENTOR(S) : Fuke Wang et al.

Page 1 of 1

It is certified that error appears in the above-identified patent and that said Letters Patent is hereby corrected as shown below:

In the Claims

At Column 30, Line 30, "rheology modifier" should be -- rheology modifier (a) --.

Signed and Sealed this
Eighth Day of July, 2025

Coke Morgan Stewart
*Acting Director of the United States Patent and Trademark Office*